(12) United States Patent
Cherukuri

(10) Patent No.: US 6,406,717 B2
(45) Date of Patent: *Jun. 18, 2002

(54) RAPID-MELT SEMI-SOLID COMPOSITIONS, METHODS OF MAKING SAME AND METHODS OF USING SAME

(75) Inventor: Subraman Rao Cherukuri, Vienna, VA (US)

(73) Assignee: Capricorn Pharma, Inc., Frederick, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/898,471

(22) Filed: Jul. 5, 2001

Related U.S. Application Data

(63) Continuation-in-part of application No. 09/610,489, filed on Jul. 5, 2000.

(51) Int. Cl.⁷ .............................. A61K 9/14; A61K 47/00

(52) U.S. Cl. ...................... 424/484; 424/405; 424/464; 514/778

(58) Field of Search .................................. 424/405, 464, 424/484, 488; 514/778

(56) References Cited

U.S. PATENT DOCUMENTS

| | | | |
|---|---|---|---|
| 4,327,076 A | 4/1982 | Puglia et al. | |
| 4,327,077 A | 4/1982 | Puglia et al. | |
| 4,446,135 A | 5/1984 | Fountaine | |
| 4,609,543 A | 9/1986 | Morris et al. | |
| 4,684,534 A | 8/1987 | Valentine | |
| 4,937,076 A | 6/1990 | Lapidus | |
| 5,320,848 A | 6/1994 | Geyer et al. | |
| 5,753,255 A | 5/1998 | Chavkin et al. | |
| 5,837,285 A | 11/1998 | Nakamichi et al. | |
| 5,840,334 A | * 11/1998 | Raiden et al. | ............... 424/464 |
| 5,989,583 A | 11/1999 | Amselem | |
| 6,024,981 A | 2/2000 | Khankari et al. | |

FOREIGN PATENT DOCUMENTS

| | | |
|---|---|---|
| GB | 2 195 891 | 4/1988 |
| GB | 2 195 892 | 4/1988 |

* cited by examiner

Primary Examiner—Thurman K. Page
Assistant Examiner—Blessing Fubara
(74) Attorney, Agent, or Firm—Nath & Associates PLLC; Gary M. Nath; Jerald L. Meyer

(57) ABSTRACT

A novel rapid-melt, semi-solid molded composition, including methods of making the same, and methods of using the same for the delivery of prophylactic and therapeutic active materials to a mammal wherein the prophylactic or therapeutic active is a psychotropic, a gastrointestinal therapeutic or a migraine therapeutic.

8 Claims, No Drawings

RAPID-MELT SEMI-SOLID COMPOSITIONS, METHODS OF MAKING SAME AND METHODS OF USING SAME

This application is a continuation-in-part application of U.S. patent application Ser. No. 09/610,489, filed Jul. 5, 2000, the entire contents of which are hereby incorporated in their entirety.

BACKGROUND OF THE INVENTION

1. Field of the Invention

The present invention relates to a rapid-melt, semi-solid composition for delivery of prophylactic and therapeutic active materials to a mammal, methods of making the same, and methods of using the same. Preferably, the therapeutic active is a antibiotic.

2. Description of the Prior Art

Pharmaceutical compositions may be produced in a variety of dosage forms, depending upon the desired route of administration of the therapeutic material and upon the particular pharmaco-therapeutic needs of the patient in need thereof.

One desired route of administration is through oral dosage forms which include solid compositions such as tablets, emulsions, and suspensions. The particular dosage form utilized will depend on such factors as the solubility and chemical reactivity of the pharmaceutical active. Further, the dosage form may be selected so as to optimize delivery of the pharmaceutical active and/or consumer acceptability of the composition.

Tablet compositions offer many advantages, including ease of product handling, chemical and physical stability, portability (in particular, allowing ready availability to the consumer when needed), aesthetic acceptability and dosage precision, i.e., ensuring consistent and accurate dosages of the pharmaceutical active. However, the pharmaco-therapeutic needs of the patient must also be taken into account.

In particular, older patients have difficulty in swallowing solid dosage forms resulting in substantial discomfort and non-compliance. The problem is aggravated by the fact that elderly patients are generally required to take a large number of drug products on a daily basis. Although tablets and capsules are sometimes coated to facilitate swallowing, the sheer number of drug products nevertheless results in substantial non-compliance and discomfort.

Pediatric patients also have difficulty swallowing until they reach the age of about 10–16 years old. Younger pediatric patients generally take either chewable tablets, crush and mix regular tablets with food/juice, or take a liquid dosage form. However, chewable tablets oftentimes possess undesirable taste properties.

One way to circumvent undesirable taste properties is by providing for confectionery tablets designed to be chewed either to provide proper flavor or to increase the surface area of a particular drug to permit rapid activity in the digestive tract or circulatory systems. However, many pharmaceutical ingredients usually have both an unpleasant mouth feel and unpalatable taste due to chalkiness, grittiness, dryness and astringent properties of these materials resulting in difficulty in swallowing. Accordingly, the practical value of these materials is substantially diminished since patients finding them objectionable may fail to take them as prescribed.

Providing the drug product in liquid dosage forms may overcome difficulty in swallowing. Liquid dosage forms are relatively easy to administer. Moreover, liquid formulations offer advantages in the treatment of certain disorders, such as disorders of the upper gastrointestinal tract, wherein delivery of an active material dissolved or dispersed in a liquid ensures rapid and complete delivery to the afflicted area. However, liquid dosage forms are more costly, easily spilled, often do not taste good, occupy large volumes of space per dosage unit, and possess some inherent stability problems. In an effort to obtain the therapeutic advantages associated with liquid formulations as well as the broad advantages associated with solids, many chewable tablet formulations have been developed.

Khankari et al., U.S. Pat. No. 6,024,981, discloses a rapidly dissolving robust dosage form directed to a hard tablet that can be packaged, stored and processed in bulk. The solid tablet dissolves in the mouth of a patient with a minimum of grit. The tablet contains an active ingredient mixed into a matrix of a non-direct compression filler and a relatively high lubricant content.

Amselem, U.S. Pat. No. 5,989,583, discloses a dry solid lipid composition suitable as an oral dosage form. The composition contains a lipophilic substance, at least one fat which is a solid at about 25° C. and at least one phospholipid present in an amount of about 2 to 40% by weight of the composition. However, the resultant product is a dry solid lipid composition.

United Kingdom patent application GB 2 195 892 discloses pharmaceutical chewable tablets with improved palatability. The lipid-containing molded tablets include a lipid material having a melting point from about 26° C. to about 37° C., a particulate dispersant material, an emulsifier and a safe and effective amount of a pharmaceutically active material. The tablets of the lipid composition exhibit improved palatability, and effective dispersion in the mouth and stomach.

United Kingdom patent application GB 2 195 891 also discloses pharmaceutical chewable tablets with improved palatability. The lipid-containing molded tablets include a lipid material, a dispersant, a nonionic emulsifier having an HLB of at least 10, and a safe and effective amount of a pharmaceutical active material, wherein the average HLB of all emulsifiers in the composition is at least about 8.

Nakamichi et al., U.S. Pat. No. 5,837,285, discloses fast soluble tablets that can be produced by a simple method. The tablet base is a sugar alcohol. The mixture of the sugar alcohol and a drug is subjected to compressive shaping prior to drying in the process. The dry solid tablet can be produced by modification of conventional tableting technology and possesses physico-chemical stability.

Chavkin et al., U.S. Pat. No. 5,753,255 discloses a chewable medicinal tablet. The tablet contains about 30 to about 95% by weight of a capric triglyceride and a medicinally active ingredient up to 60% by weight. If the medicinally active ingredient is less than about 30% by weight, then the composition also contains up to 10% by weight of a member of the group consisting of glyceryl monostearate, a mixture of glyceryl monostearate and glyceryl monopalmitate, and a mixture of glyceryl monostearate and glyceryl distearate.

Geyer et al., U.S. Pat. No. 5,320,848, discloses a non-aqueous chewable composition for oral delivery of unpalatable drugs. The drug is intimately dispersed or dissolved in a pharmaceutically-acceptable lipid that is solid at room temperatures. The lipid material desirably readily melts with the application of mild temperatures, i.e. about 55 to 95° C.

Lapidus, U.S. Pat. No. 4,937,076, discloses a chewable aspirin and buffering material tablet in a single dosage form.

The buffering materials are integrally dispersed and bound in a fatty material of chocolate, synthetic chocolate or hydrogenated tallow. The fatty material individually coats the aspirin and buffering material.

Valentine, U.S. Pat. No. 4,684,534, discloses quick-liquefying, chewable tablets. The tablets have a harder outer shell which inhibits penetration of liquid, and a softer interior which quickly liquefies when the tablet and shell are broken into pieces and contacted by the liquid. The excipient or base material of the tablet is made from carbohydrates held together with small quantities of a carbohydrate binder such as maltodextrin. The tablets can contain active ingredients such as pharmaceuticals, breath sweeteners, vitamins and dietary supplements.

Morris et al., U.S. Pat. No. 4,609,543, discloses a soft homogeneous antacid tablet. The tablet contains solid antacid particles thoroughly coated with a mixture composed of a fatty material or oil, a surfactant, and a flavor. The fat or oil is present in an amount of from about 25% to about 45% of the mixture. The primary particle size of the antacid is less than 100 millimicrons.

Fountaine, U.S. Pat. No. 4,446,135, discloses chewable calcium carbonate-containing antacid tablets having good mouth feel properties. The good mouth feel properties of the tablet are obtained by using calcium carbonate of a particular particle size in combination with certain excipients. The calcium carbonate is present in an effective amount and has a size from about 5 to 50 microns in diameter.

Puglia et al., U.S. Pat. No. 4,327,077, discloses a compressed chewable antacid tablet which has good flexibility, is breakage resistant and disintegrates immediately upon chewing. The tablet is formed of a recrystallized fatty material, such as chocolate, a bulking material and an active ingredient bound up in the particles of the recrystallized fatty material. The preferred recrystallized fatty material is a chocolate or a synthetic chocolate.

Puglia et al., U.S. Pat. No. 4,327,076, also discloses a compressed chewable antacid tablet which has good flexibility, is breakage resistant and disintegrates immediately upon chewing. The tablet is formed of particles of the antacid or other active ingredient which are admixed with particles formed of edible fat or oil absorbed on a fat-absorbing material, such as microcrystalline cellulose. Upon chewing, the tablet is quickly converted to a smooth creamy non-gritty palatable emulsion.

However, the prior art compositions contain various disadvantages. For example, tablets may be incompletely chewed due to the poor palatability of the composition. Such compositions may also have a gummy texture, and are subject to "taste fatigue," i.e., the composition is perceived to be less palatable after ingestion of multiple doses. Further, the binders and other materials used in such chewable tablets may prevent rapid and effective delivery of active materials to the stomach.

There is a need for a rapid-melt, semi-solid composition that behaves like a liquid when consumed by a mammal, and yet acts like a solid in many other ways. The need extends for compositions in which no biting or chewing is necessary in order for the composition to melt in the mouth of a mammal. Such compositions are ideal for uses in the fields of pediatric and geriatric care, that is, for use with people or mammals that do not have any teeth.

It has been found that semi-solid product formulations containing one or more certain lipid materials, emulsifiers and particulate materials are highly palatable and effective compositions for the delivery of pharmaceutical active materials. Such compositions afford better taste, mouth feel and storage stability than those compositions known in the art.

BRIEF SUMMARY OF THE INVENTION

Applicant has unexpectedly developed a novel rapid-melt, semi-solid molded composition comprising:

at least one binder in an amount from about 0.01% to about 70% by weight;

a salivating agent in an amount from about 0.05% to about 15% by weight;

a diluent/bulking material in an amount from about 10% to about 90% by weight; and a therapeutically effective amount of an antibiotic.

Applicant has further developed a novel method of preparing a rapid-melt, semi-solid molded composition comprising the steps of:

a) melting at least one binder in an amount from about 0.01% to about 70% by weight with a salivating agent in an amount from about 0.05% to about 15% by weight, to form a mixture;

b) mixing a therapeutically effective amount of an antibiotic with said mixture to form an active mixture;

c) mixing a diluent/bulking material with said active mixture to form a final mixture; and d) molding said final mixture into said rapid-melt, semi-solid molded composition.

Further, Applicant has unexpectedly developed a novel method for treating a bacterial infection comprising the step of administering to a geriatric or pediatric patient in need thereof a pharmaceutical composition comprising:

at least one binder in an amount from about 0.01% to about 70% by weight;

a salivating agent in an amount from about 0.05% to about 15% by weight;

a diluent/bulking material in an amount from about 10% to about 90% by weight;

a therapeutically effective amount of an antibiotic.

The rapid-melt, semi-solid molded compositions of the present inventive subject matter exhibit good resistence to prolonged exposure to heat and the atmosphere. More particularly, the compositions surprisingly maintain their texture and rapid melting properties when exposed to those elements.

DETAILED DESCRIPTION OF THE EMBODIMENTS

The rapid-melt, semi-solid molded compositions of the present inventive subject matter contains at least one binder, a salivating agent, an active material, and a diluent/bulking material. The rapid-melt, semi-solid compositions may also contain a slipping agent to aid in the transport of the composition from the mouth of the mammal to the stomach thereof.

As used herein, the expression "mammal" includes without limitation any mammalian subject, such as mice, rats, guinea pigs, cats, dogs, human beings, cows, horses, sheep or other livestock.

As used herein, the expression "free water" means water that is not found in other ingredients. Many ingredients used in the present inventive compositions may also have water as part of the ingredient, and the term "free water" refers to water that is separate from those ingredients.

The unique novel combination of elements allows for fast melting of the composition when placed in the mouth of a user. By pressing the composition between the tongue and cheek of the user, the saliva of the user provides hydration to the composition and allows the composition to melt without any chewing. A unique feature of the present inventive compositions is that the composition becomes a liquid upon the application of pressure. The semi-solid compositions rapidly melt upon the application of pressure by the tongue of the patient, thus forming a liquid carrier for the active ingredients contained therein. The liquid helps provide the unique characteristics and features of the present inventive compositions.

The liquification of the inventive compositions can be achieved through the application of pressure by the tongue of the patient, as described above. Optionally, the liquification may be attained by the patient chewing the compositions. A slight amount of chewing will enhance the liquefication of the compositions. A further way for the composition to be liquified is by the patient sucking on the rapid-melt, semi-solid compositions of the inventive subject matter.

The rapid-melt, semi-solid technology of the present inventive subject matter has multiple applications which are ideal for the unique properties of the compositions. One such application is the delivery of active ingredients to a mammal in need thereof.

In addition, the melting feature of the novel compositions makes the compositions ideal for uses in pediatric and geriatric care. By rapidly melting, the compositions facilitate swallowing, improve taste, and increase patient compliance by decreasing the number of pills taken daily. In particular, the novel compositions circumvent the need to crush and mix tablets with food/juice or the need for costly, easily spilled and voluminous liquid dosage forms. With this intended use in mind, the compositions may be specially formulated for pediatric and geriatric patients.

The unique properties further aid in drug compliance of geriatric and pediatric patients because the drugs may be administered in a way that will not require chewing by the patient. In particular, the novel compositions reduce discomfort associated with chewable dosage forms such as chalkiness, grittiness, dryness and astringent properties. Furthermore, the rapid melt compositions allow complete and rapid delivery of an active material in an afflicted area.

Another application for which the inventive compositions are ideal is to enhance the saliva flow of a patient. A frequent problem for geriatric patients is dry-mouth, or the inability to salivate sufficiently. The aid of saliva flow by the use of the present inventive compositions will enhance tooth cleaning within the patient, as well as stimulate better drug delivery to the patient. Also, the increased saliva flow will facilitate better breath characteristics in the patient. The use of xylitol, as well as other polyols and sugars, in the inventive compositions will contribute to the enhancement of the saliva flow of the patient.

A further application for the inventive compositions would be the preparation of compositions for drug delivery in diabetic patients. A diabetic patient must monitor the intake of sugar and the ability to formulate the present inventive compositions with fructose and other non-cariogenic components makes them ideal for delivery of drugs to diabetic patients.

The rapid-melt, semi-solid compositions of the present inventive subject matter are preferably anhydrous, that is, they do not contain any water. The lack of water in the inventive compositions allows high doses of active materials or combinations of active materials to be incorporated into the compositions due to the stability of the active materials in the absence of the water. It is contemplated, however, that the compositions may optionally include an amount of water. The amount of water present will depend on the active ingredients to be delivered, but generally will be present in an amount less than 2.0% by weight of the composition. Preferably, the water will be present in an amount less than 1.0% by weight of the composition.

The rapid-melt, semi-solid compositions of the present inventive subject matter contain at least one binder. As used herein, "binder" means at least one ingredient useful in keeping the composition in its semi-solid state, may be either solid or liquid, and may include, without limitation, a high melting point fat or waxy material such as lipid materials, polyethylene glycols (PEG), waxes and other fats. Preferably, the semi-solid compositions of the present inventive subject matter contains a mixture of binders. The solid binders useful in the compositions of the present inventive subject matter have a melting point of about 25 to 90° C., and preferably about 37° C. When more than one binder is used in the inventive compositions, the melting point of the combination of the binders will remain within the range of 25 to 90° C., and preferably about 37° C. The inventive subject matter contemplates the use of mixtures of solid binders and liquid binders. For a non-limiting example, the present inventive subject matter contemplates mixing a small amount of a high-melting point lipid with a liquid binder to achieve a binder that attains the desired product characteristics. These characteristics include such factors as mouth feel, rapidity of melting in the mouth, appearance, flavor and compatibility with active materials and therapeutic active materials.

Among the lipid materials useful as binders in the compositions of the present inventive subject matter are those which are commercially available and commonly used in confectionery and other food products. Such lipid materials include, without limitation, cocoa butter, hydrogenated tallow, hydrogenated vegetable oils, hydrogenated cotton seed oil, palm kernel oil, soybean oil, stannol esters, and derivatives and mixtures thereof. Hydrogenated vegetable oils (such as hydrogenated palm kernel oil), cocoa butter, and cocoa butter substitutes are among the preferred useful lipid materials.

Other materials are also suitable as binders in the present inventive subject matter. Included within the materials suitable as binders are, without limitation, polyethylene glycols and liquid binders. Examples of liquid binders are, without limitation, poly saccharides, gum solutions, water, corn syrup, hydrogenated starch hydrolates, glycerine, polypropylene glycol, and mixtures thereof.

The amount of binder present in the rapid-melt, semi-solid molded composition of the present inventive subject matter is from about 0.01% to about 70% by weight of the final composition. Preferably, the amount of binder is from about 0.01% to about 50% by weight of the composition. More preferably the binder is present from about 15% to about 30% by weight of the composition.

The binder is used to provide good melt away properties to the composition while preventing a gritty texture being imparted by the composition. The binder aids in the fast melting of the composition when placed in the mouth of a user.

The rapid-melt, semi-solid molded composition of the present inventive subject matter also contains a salivating agent. As is used herein, "salivating agent" means a material that promotes greater salivation in the user of the compositions of the present inventive subject matter. The salivating agent helps create salivation in the mouth of the mammal using the inventive compositions. This is an important feature since the present compositions are intended to be taken by the patient without the aid of water to help in the transporting of the composition to the stomach of the patient. The salivating agent can be, without limitation, an emulsifier or a food acid that initiates salivation in the mouth of the patient.

Examples of emulsifiers useful as salivating agents in the compositions of the present inventive subject matter include, without limitation, alkyl aryl sulfonates, alkyl sulfates, sulfonated amides and amines, sulfated and sulfonated esters and ethers, alkyl sulfonates, polyethoxlyated esters, mono- and diglycerides, diacetyl tartaric esters of monoglycerides, polyglycerol esters, sorbitan esters and ethoxylates, lactylated esters, phospholipids such as lecithin, polyoxyethylene sorbitan esters, proplyene glycol esters, sucrose esters, and mixtures thereof. The emulsifier may be either saturated or unsaturated.

Examples of food acids useful as salivating agents in the inventive compositions include, without limitation, citric acid, malic acid, tartarate, food salts such as sodium chloride and salt substitutes, potassium chloride, and mixtures thereof.

The amount of salivating agent present in the rapid-melt, semi-solid molded composition of the present inventive subject matter is from about 0.05% to about 15% by weight of the final composition. Preferably, the amount of salivating agent from about 0.3% to 0.4% by weight of the composition.

Keeping the amount of salivating agent present in the inventive composition within these limits for weight percentage is important to enhance the desirable properties of the compositions. More particularly, the low amount of salivating agent present in the compositions aid in the compositions retaining the semi-solid state and the rapidity of melting in the mouth of a mammal.

The rapid-melt, semi-solid molded compositions of the present inventive subject matter further contain a diluent/bulking material. The use of a diluent/bulking material is necessary to serve as a free-flow imparting agent which aids in the moisturizing of the composition when chewed, that is, the diluent/bulking material aids in the processability of the compositions. The diluent/bulking material also serves to reduce the concentration of the active materials and add bulk to the composition. Examples of diluent/bulking materials useful in the compositons of the present inventive subject matter include, without limitation, silicon dioxide, sugars, starches, lactose, sucrose, sorbitol, fructose, talc, stearic acid, magnesium stearate, dicalcium phosphate, erythitol, xylitol, mannitol, maltitol, isomalt, dextrose, maltose, lactose, microcrystalline celluloses and mixtures thereof.

The amount of diluent/bulking material present in the semi-solid molded compositions is from about 10% to about 90% by weight of the final composition. Preferably, the amount of diluent/bulking material is from about 35% to about 55% by weight of the final composition.

The rapid-melt, semi-solid compositions of the present inventive subject matter may optionally contain a further slipping agent to aid in the palatability of the composition after it melts in the mouth of the mammal. The slipping agent may be a further lipid material, as is described above for binders, or another material which aids in the "slipping" of the composition through the mouth and down the esophagus of the mammal.

As is discussed above, the preferably anhydrous nature of the present inventive compositions allows for very high doses of active materials to be incorporated therein. The amount of active material present in the inventive compositions will vary depending on the particular active used, but generally will be present in an amount of about 0.001% to 70% by weight of the composition. Preferably, the active ingredients used in the inventive compositions are prophylactic or therapeutic active ingredients. Prophylactic or therapeutic active materials which can be used in the present invention are varied. A non-limiting list of such materials includes the following: antitussives, antihistamines, decongestants, alkaloids, mineral supplements, laxatives, vitamins, antacids, ion exchange resins, anti-cholesterolemics, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidrrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypontics, anti-emetics, anti-nausants, anti-convulsants, neuromuscular drugs, hyper- and hypoglycemic spasmodics, uterine relaxants, mineral and nutritional additives, antiobesity drugs, anabolic drugs, erythropoetic drugs, antiashmatics, cough suppressants, mucolytics, anti-uricemic drugs and mixtures thereof.

Preferred prophylactic or therapeutic active materials contemplated for use in the present inventive subject matter are analgesics. Examples of analgesics useful in the present inventive subject matter, and which are the preferred therapeutic active ingredients, include, without limitation, aspirin, acetaminophen, ibuprophen and mixtures thereof.

Another preferred active material can be selected from the class antibiotics including beta-lactamse inhibitor, quinolone, macrolide, cephalosporin, glycopeptide, cephem, imunoglobin tetracycline, fluoroquinolone aminoglycoside, and monobactum antibiotics.

Examples of some antibiotics include amoxicillin and clavulanate potassium, ciprofloxacin HCl, azithromycin, clarithromycin, sterile ceftriaxone sodium, cefuroxime axetil, imipenem cilastatin, levofloxacin, ceftazidime, ampicillin sodium and sulbactum sodium, cefaclor, amoxicillin, cefdinir, roxithromycin, sterile cefotaxime sodium, vancomycin, piperacillin sodium and tazobactum sodium, morniflumate, flomoxef sodium, cefotiam dihydrochloride, ofloxacin, mupirocin calcium, vancomycin HCl, teicoplanin, cefadroxil monohydrate, sulbactum cefoperazone, meropenem, ofloxacin, cephalexin, cefepime HCl, cefuroxime sodium, minocycline HCl, cefaclor, cefazolin, trimethoprim and sulfamethoxazole, norfloxacin, trovafloxacin, cefpodoxime proxetil, cefdinir, cefixime, panipenem, ceftibuten, levofloxacin, cefoxopran HCl, amikacin sulfate, aztreonam, minocycline HCl, ticarcillin disodium or mixtures thereof.

In general, any antibiotic indicated for bacterial infections may be used in the present invention. For example, amoxicillin and clavulanate potassium may be incorporated into the rapid-melt semi-solid compositions of the present invention to effectively deliver amoxicillin and clavulanate potassium to a patient in need thereof. In particular, amoxicillin and clavulanate potassium can be formulated with the present invention in doses ranging from about 30 to 500 mg amoxicillin in combination with about 15 to 75 mg clavulanate potassium. All the examples are non-limiting and it will be understood that other antibiotics may be used with the present inventive subject matter.

Yet another active material used in the compositions of the present invention are anti-diarrheal therapeutics. Anti-diarrheal therapeutics treat the condition of diarrhea whether it is symptomatic of the disorder itself wherein diarrhea is a condition that occurs when a mammal has a low amount of stool in a bowel movement. Diarrhea results mainly from excess fecal water in the bowel of the mammal. Specific examples of anti-diarrheal therapeutics include loperamide HCl, diphenoxylate, codeine phosphate, camphorated opium tincture.

The present inventive subject matter contemplates incorporating loperamide hydrochloride into the rapid-melt semi-solid compositions as an effective means of delivering the active to a patient in need thereof. The amount of loperamide hydrochloride needed in the will depend on the intended recipient of the active ingredient. The normal dosage amount for a human adult is initially 4 milligrams, with a follow-up dosage of 2 milligrams after each unformed stool. For children, the normal dosage will depend on the age and weight of the child, pursuant to the guidelines set forth by the child's physician.

The use of the present inventive subject matter to deliver loperamide hydrochloride to a child is especially effective since the rapid-melt, semi-solid compositions of the present inventive subject matter do not require any chewing by the patient. As has been previously explained, the melting feature of the novel compositions makes the compositions ideal for uses in pediatric and geriatric care, since small children and aged individuals often have difficulty chewing items. With this intended use in mind, the compositions may be specially formulated for pediatric and geriatric patients. The unique properties will aid in drug compliance by such patients as the drugs may be administered in a way that will not require chewing by the patient.

Further preferred nutritional active materials useful in the present inventive subject matter include, without limitation, calcium-containing materials such as calcium carbonate, vitamins, minerals, herbals, spices and mixtures thereof.

Examples of vitamins that are available as active ingredients include, without limitation, vitamin A (retinol), vitamin D (cholecalciferol), vitamin E group (α-tocopherol and other tocopherols), vitamin K group (phylloquinones and menaquinones), thiamine (vitamin $B_1$), riboflavin (vitamin $B_2$), niacin, vitamin $B_6$ group, folic acid, vitamin $B_{12}$ (cobalamins), biotin, vitamin C (ascorbic acid), and mixtures thereof. The amount of vitamin or vitamins present in the final encapsulated product of the present inventive subject matter is dependent on the particular vitamin and is generally the United States' Department of Agriculture Recommended Daily Allowances (USRDA) for that vitamin. For example, if vitamin C is the active ingredient and the encapsulated product is being used in a confectionery or chewing gum targeting adults, the amount of vitamin C in the encapsulated product would be 60 milligrams, which is the USRDA of vitamin C for adults.

Examples of minerals that are available as active ingredients include, without limitation, calcium, magnesium, phosphorus, iron, zinc, iodine, selenium, potassium, copper, manganese, molybdenum and mixtures thereof. As is the case with vitamins, the amount of mineral or minerals present in the final encapsulated product of the present inventive subject matter is dependent on the particular mineral and is generally the USRDA for that mineral. For example, if iodine is the active ingredient and the encapsulated product is being used in a confectionery or chewing gum targeting adults, the amount of iodine in the encapsulated product would be 150 micrograms, which is the USRDA of iodine for adults.

Examples of herbals that are available as active ingredients include, without limitation, echinacea, peppermint, licorice, goldenseal, panax pseudoginseng, grapeseed extract, bilberry, kava, ginko biloba, panax quinquefolium, Siberian ginseng, St. John's wort, bromelian, guglupids, hawthorn, garlic, ginger, angelica species, dandelion, goldenseal, and mixtures thereof. Further, examples of spices that are available as active ingredients include, without limitation, mustard, dillweed, cinnamon, garlic, black pepper, onion, sage, oregano, basil, cream of tartar, targon, cayenne pepper, red pepper, and mixtures thereof. This list of herbals and spices is for exemplary purposes and is not meant to be construed as limiting the inventive subject matter thereto.

Many of the active material listed above have unpalatable tastes. Taste-masking of compositions with those unpalatable active materials is well-known in the art. The use of flavors and sweeteners to mask the unpalatability of the active materials is also well-known.

Thus, other materials which can be incorporated into the rapid-melt, semi-solid molded composition of the present inventive subject matter include flavors, colors and sweeteners. A distinct feature of the inventive rapid-melt, semi-solid compositions is that they exhibit excellent taste characteristics. Importantly, it is possible to incorporate high levels of flavors, sweeteners and other taste-masking agents, making the compositions more palatable when undesirable tastes accompany the active materials.

Flavors may be chosen from natural and synthetic flavor liquids. Flavors useful in the present inventive compositions include, without limitation, volatile oils, synthetic flavor oils, flavoring aromatics, oils, liquids, oleoresins or extracts derived from plants, leaves, flowers, fruits, stems and combinations thereof. A non-limiting list of examples include citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral, i.e., alphacitral (lemon, lime), neral, i.e., betal-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), and mixtures thereof.

Further examples of flavors useful in the inventive compositions include, without limitation, beef flavorings, chicken flavorings, rice flavorings, lamb flavorings, pork flavorings, seafood flavorings, and mixtures thereof.

The sweeteners may be chosen from the following non-limiting list: flucose (corn syrup), dextrose, invert sugar, fructose, and mixtures thereof; saccharin and its various salts such as the sodium salt; dipeptide sweeteners such as aspartame; dihydrochalcone compounds, glycyrrhizin; Stevia rebaudiana (Stevioside); chloro derivatives of sucrose such as sucralose; sugar alcohols such as sorbitol, mannitol, zylitol, and the like. Also contemplated are hydrogenated starch hydrolysates and synthetic sweetener 3,6-dihydro-6-methyl-1-1-1,2,3-oxathiazin-4-one-2,2-dioxide, particularly the potassium salt (acesulfame-K) and sodium and calcium salts thereof. Other sweeteners may also be used.

The rapid-melt, semi-solid compositions of the present inventive subject matter may also be coated in order to facilitate handling of the compositions. Coatings well-known in the art are useful for keeping the compositions from melting prior to being administered to a patient in need of an active material. By coating the compositions, the composition will maintain its semi-solid state while being handled and will melt when inserted into a patient's mouth.

The present inventive subject matter also contemplates a method of preparing a rapid-melt, semi-solid molded composition. It should be recognized that the composition may be prepared by a variety of methods well-known by those of ordinary skill in the art. Such processes may be used on a batch or continuous process format and would involve melting the binders and uniformly blending them for suitable periods of time prior to adding the salivating agent. Once these two components have been blended together, the further components may be added either together or sequentially until a uniform mixture is obtained. It should be recognized that the resulting mixture should be in a semi-solid state that may be poured into a mold, cast into preformed shapes, or stamped into the final products. Clearly, other tableting techniques are contemplated to be used herein.

A particularly preferred method involves the steps of: melting at least one binder having a melting point about 25 to 45° C. with a salivating agent to form a mixture; mixing an active material with the lipid material to form an active mixture; mixing a diluent/bulking material with said active material to form a final mixture; and molding the final mixture into the semi-solid molded composition. The method of the present inventive subject matter also contemplates adding other materials to the final mixture prior to molding into the semi-solid molded composition. Other materials which may be added to the final mixture prior to molding include, without limitation, flavors, colors, sweeteners, and mixtures thereof.

The amount of binder melted with the salivating agent is from about 10% to about 70% by weight of the final composition. Preferably, the amount of binder is from about 10% to about 50% by weight. More preferably the binder is present from about 15% to about 30% by weight. Likewise, the amount of salivating agent melted in the first step of the method is from about 0.2% to about 0.5% by weight of the final composition. Preferably, the amount of salivating agent is from about 0.3% to 0.4% by weight of the composition.

The rapid-melt, semi-solid compositions of the present inventive subject matter produced by the above methods have increased product integrity and stability. The compositions are "storage stable", meaning that the compositions are stable in the absence of special handling procedures. The inventive compositions are stable both prior to packaging and after packaging. Importantly, the inventive compositions maintain their stability and integrity without refrigeration and without humidity controls being implemented during handling, packaging and storing of the products. Additionally, since the compositions exhibit increased integrity and stability, the compositions can be used in most of the current economical packages suitable for a global environment. Further, high temperatures are not needed when processing the inventive compositions. The only heat that needs to be used during processing is to melt the binder prior to mixing with the other elements.

The following examples are illustrative of preferred embodiments of the invention and are not to be construed as limiting the invention thereto. All percentages are given in weight percent, unless otherwise noted and equal a total of 100%.

EXAMPLES

Example #1

Preparation of 25% Calcium Carbonate Semi-solid Molded Composition 60.00 grams of cocoa butter was melted with 0.80 grams of lecithin and 2.00 grams of sorbitan monostearate. 0.2 grams of yellow #5 was added to the above mixture after the ingredients had completely melted. To this mixture was added 50.00 grams of calcium carbonate. The mixture was then mixed for approximately three minutes. Following the mixing period, 85.80 grams of sugar and 0.80 grams of liquid peppermint flavor was added to the mixture to form 200.00 grams of the final mixture. The final mixture was mixed for approximately 5 minutes, until all of the ingredients had been thoroughly mixed.

The final mixture was molded into the final product and allowed to set-up. The resultant product contained 25% calcium carbonate.

Example #2

Preparation of 31.50% Calcium Carbonate Semi-solid Molded Composition 30.00 grams of cocoa butter was melted with 0.6 grams of lecithin and 2.00 grams of sorbitan monstearate. 0.60 grams of red #4 was added after the ingredients had completely melted. 0.20 grams of polyoxyethylene sorbitol monostearate was then added to the mixture and the mixture was mixed for 3 minutes. To this mixture was added 31.50 grams of calcium carbonate and the mixture was further mixed for another 3 minutes. Following the mixing period, 51.30 grams of xylitol powder was added to the mixture along with 0.80 grams of cherry flavor and 0.60 grams of vanilla extract, forming 200.00 grams of final mixture. The final mixture was mixed for approximately 5 minutes, until all of the ingredients had been thoroughly mixed.

The final mixture was molded into the final product and allowed to set-up. The resultant product contained 31.50% calcium carbonate.

Example #3

Preparation of 31.50% Calcium Carbonate Semi-solid Molded Composition 38.00 grams of cocoa butter was melted with 0.68 grams of lecithin and 2.00 grams of sorbitan monstearate. 0.16 grams of red #40 was added after the ingredients had completely melted. The mixture was mixed for 8 minutes at 120° F. 0.40 grams of polyoxyethylene sorbitan ester, 0.40 grams of polyglycerol ester, and 4.00 grams of glycerine (99.7%) were added to the mixture and the mixture was further mixed for 2 minutes at 110°. To this mixture was added 63.00 grams of calcium carbonate and the mixture was further mixed for another 4 minutes. Following the mixing period, 4.00 grams of polyethylene glycol, 85.46 grams of sugar 10×, 0.18 grams of aspartame and 0.12 grams of acesulfame K were added to the mixture and the resultant mixture was mixed for 4 minutes at 90–110° F. The mixture was removed rom the heat and 0.40 grams of vanilla flavoring and 1.20 grams of strawberry flavoring was added to the mixture, resulting in 200.00 grams of mixture. The final mixture was mixed for approximately 5 minutes, until all of the ingredients had been thoroughly mixed.

The final mixture was molded into the final product and allowed to set-up. The resultant product contained 31.50% calcium carbonate.

Example #4

Preparation of 31.50% Calcium Carbonate Semi-solid Molded Composition 38.00 grams of cocoa butter, 0.80 grams of lecithin, 0.40 grams of polyoxyethylene sorbitan ester, 2.00 grams of sorbitan monostearate, 6.00 grams of polyethylene glycol, 0.16 grams of red #40, and 4.00 grams of glycerine were mixed at 130° F. for 8 minutes. 63.00 grams of calcium carbonate was added and the mixture was continuously mixed until the calcium carbonate had completely dissolved at 130° F. 84.04 grams of xylitol and 1.6 grams of strawberry flavor were added, resulting in 200.00 grams of the final mixture. The mixture was mixed for 10 minutes, until all of the ingredients had been thoroughly mixed.

The final mixture was molded into the final product and allowed to set-up. The resultant product contained 31.50% calcium carbonate.

Example #5

Preparation of 31.50% Calcium Carbonate Semi-solid Molded Composition 38.00 grams of cocoa butter, 0.68 grams of lecithin, 2.00 grams of sorbitan monostearate, and 0.16 grams of red #40 were mixed at 100° F. for 8 minutes. 4.00 grams of polyethylene glycol and 0.40 grams of polyoxyethylene sorbitan ester was added to the mixture. The mixture was mixed for 2 minutes at 110° F. for 2 minutes. 0.40 grams of polyglycerol ester and 63.00 grams of calcium carbonate were then added and the mixture was mixed for 4 minutes at 90° F. 0.18 grams of aspartame, 0.12 grams of acesulfame K and 89.66 grams of sugar 10× were added and the mixture was mixed for 8 minutes at 90° F. The mixture was removed from the heat and 1.00 gram of strawberry flavoring and 0.40 grams of vanilla flavorings were added, resulting in 200.00 grams of final mixture. The mixture was mixed for 10 minutes, until all of the ingredients had been thoroughly mixed.

The final mixture was molded into the final product and allowed to set-up. The resultant product contained 31.50% calcium carbonate.

Example #6

Preparation of 31.50% Calcium Carbonate Semi-solid Molded Composition 30.0 grams of cocoa butter were mixed with 0.6 grams of lecithin. The mixture was heated to 90° F. for 3 minutes. 2.0 grams of sorbitan monostearate, 0.2 grams of polyoxyethylenee sorbitan ester, and 4.0 grams of polyethylene glycol were added to the mixture. The mixture was mixed for 2 minutes at 110° F. 63.0 grams of calcium carbonate was added and the mixture was thoroughly mixed for 10 minutes. 49.1 grams of sugar 10×, 0.3 grams of aspartame and 49.1 grams of mannitol were added and the mixture was mixed until all ingredients were thoroughly mixed. 0.1 grams of red #40, 0.6 grams of vanilla flavoring and 1.0 grams of strawberry flavoring were added to the mixture, resulting in 200.0 grams of final mixture. The mixture was mixed for 10 minutes, until all of the ingredients had been thoroughly mixed.

The final mixture was molded into the final product and allowed to set-up. The resultant product contained 31.50% calcium carbonate.

Example #7

Preparation of 31.50% Calcium Carbonate Semi-solid Molded Composition 30.0 grams of cocoa butter were mixed with 0.6 grams of lecithin. The mixture was heated to 90° F. for 3 minutes. 2.0 grams of sorbitan monostearate, 0.2 grams of polyoxyethylenee sorbitan ester, and 4.0 grams of polyethylene glycol were added to the mixture. The mixture was mixed for 2 minutes at 110° F. 63.0 grams of calcium carbonate was added and the mixture was thoroughly mixed for 10 minutes. 98.1 grams of xylitol and 0.3 grams of aspartame were added and the mixture was mixed until all ingredients were thoroughly mixed. 0.2 grams of red #40, 0.6 grams of vanilla flavoring and 1.0 grams of strawberry flavoring were added to the mixture, resulting in 200.0 grams of final mixture. The mixture was mixed for 10 minutes, until all of the ingredients had been thoroughly mixed.

The final mixture was molded into the final product and allowed to set-up. The resultant product contained 31.50% calcium carbonate.

Example #8

Preparation of 13.47% Acetaminophen Semi-solid Molded Composition 38.00 grams of cocoa butter, 0.80 grams of lecithin and 2.00 grams of sorbitan monostearate were melted. 6.00 grams of polyethylene glycol, 4.00 grams of glycerine and 0.40 grams of polyoxyethylene sorbitan ester were added to the melt. The mixture was mixed for 6 minutes at 130° F., then for another 2 minutes at 120° F. 120.80 grams of xylitol were added to the mixture and mixed for 5 minutes at 120° F. 26.94 grams of microencapsulated acetaminophen (coated, 90% acetaminophen) were added to the mixture and the mixture was mixed for 7 minutes. 0.16 grams of red #40, 0.40 grams of vanilla flavoring and 0.80 grams of strawberry flavoring were added to the mixture, resulting in 200.30 grams of final mixture. The mixture was mixed for 10 minutes, until all of the ingredients had been thoroughly mixed.

The final mixture was molded into the final product and allowed to set-up. The resultant product contained 13.47% acetaminophen.

Example #9

Preparation of 13.57% Acetaminophen Semi-solid Molded Composition 38.00 grams of cocoa butter, 0.68 grams of lecithin and 2.00 grams of sorbitan monostearate were melted. 4.00 grams of polyethylene glycol, 4.00 grams of glycerine and 0.40 grams of polyoxyethylene sorbitan ester were added to the melt. The mixture was mixed for 6 minutes at 130° F., then for another 2 minutes at 120° F. 122.06 grams of sugar 10×, 0.18 grams of aspartame and 0.12 grams of acesulfame K were added to the mixture and mixed for 5 minutes at 120° F. 27.14 grams of microencapsulated acetaminophen (coated, 90% acetaminophen) were added to the mixture and the mixture was mixed for 7 minutes. 0.16 grams of red #40, 0.40 grams of vanilla flavoring and 0.80 grams of strawberry flavoring were added to the mixture, resulting in 199.94 grams of final mixture. The mixture was mixed for 10 minutes, until all of the ingredients had been thoroughly mixed.

The final mixture was molded into the final product and allowed to set-up. The resultant product contained 13.57% acetaminophen.

Example #10

Preparation of 13.57% Acetaminophen Semi-solid Molded Composition 38.00 grams of cocoa butter, 0.68 grams of lecithin and 2.00 grams of sorbitan monostearate were melted. 4.00 grams of polyethylene glycol and 0.40 grams of polyoxyethylene sorbitan ester were added to the melt. The mixture was mixed for 8 minutes at 120° F., then for another 2 minutes at 110° F. 125.94 grams of xylitol, 0.18 grams of aspartame and 0.12 grams of acesulfame K were added to the mixture and mixed for 5 minutes at 120° F. 27.14 grams of microencapsulated acetaminophen (coated, 90% acetaminophen) were added to the mixture and the mixture was mixed for 7 minutes. 0.16 grams of red #40, 0.40 grams of vanilla flavoring and 0.80 grams of strawberry flavoring were added to the mixture, resulting in 199.82 grams of final mixture. The mixture was mixed for 10 minutes, until all of the ingredients had been thoroughly mixed.

The final mixture was molded into the final product and allowed to set-up. The resultant product contained 13.57% acetaminophen.

Example #11

Preparation of 13.57% Acetaminophen Semi-solid Molded Composition 190.00 grams of cocoa butter, 3.40 grams of lecithin and 10.00 grams of sorbitan monostearate were melted. 20.00 grams of polyethylene glycol and 2.00 grams of polyoxyethylene sorbitan ester were added to the melt. The mixture was mixed for 8 minutes at 120° F., then for another 2 minutes at 110° F. 629.70 grams of xylitol, 0.9 grams of aspartame and 0.6 grams of acesulfame K were added to the mixture and mixed for 5 minutes at 120° F. 135.70 grams of microencapsulated acetaminophen (coated, 90% acetaminophen) were added to the mixture and the mixture was mixed for 7 minutes. 0.8 grams of red #40, 2.00 grams of vanilla flavoring and 4.00 grams of strawberry flavoring were added to the mixture, resulting in 999.10 grams of final mixture. The mixture was mixed for 10 minutes, until all of the ingredients had been thoroughly mixed.

The final mixture was molded into the final product and allowed to set-up. The resultant product contained 13.57% acetaminophen.

Example #12

Preparation of 2.17% Acetaminophen Semi-solid Molded Composition 38.00 grams of cocoa butter, 0.68 grams of lecithin and 2.00 grams of sorbitan monostearate were melted. 4.00 grams of polyethylene glycol, 0.40 grams of polyglycerol ester, 4.00 grams of glycerine and 0.40 grams of polyoxyethylene sorbitan ester were added to the melt. The mixture was mixed for 8 minutes at 120° F., then for another 2 minutes at 110° F. 143.52 grams of sugar 10×, 0.18 grams of aspartame and 0.12 grams of acesulfame K were added to the mixture and mixed for 5 minutes at 120° F. 4.34 grams of microencapsulated acetaminophen (coated, 90% acetaminophen) were added to the mixture and the mixture was mixed for 7 minutes. 0.16 grams of red #40, 0.40 grams of vanilla flavoring and 1.20 grams of strawberry flavoring were added to the mixture, resulting in 199.40 grams of final mixture. The mixture was mixed for 10 minutes, until all of the ingredients had been thoroughly mixed.

The final mixture was molded into the final product and allowed to set-up. The resultant product contained 2.17% acetaminophen.

Example #13

Preparation of 4.34% Acetaminophen Semi-solid Molded Composition 38.00 grams of cocoa butter, 0.68 grams of lecithin and 2.00 grams of sorbitan monostearate were melted. 4.00 grams of polyethylene glycol and 0.40 grams of polyoxyethylene sorbitan ester were added to the melt. The mixture was mixed for 8 minutes at 120° F., then for another 2 minutes at 110° F. 144.38 grams of sugar 10×, 0.18 grams of aspartame and 0.12 grams of acesulfame K were added to the mixture and mixed for 5 minutes at 120° F. 8.69 grams of microencapsulated acetaminophen (coated, 90% acetaminophen) were added to the mixture and the mixture was mixed for 7 minutes. 0.16 grams of red #40, 0.40 grams of vanilla flavoring and 1.00 grams of strawberry flavoring were added to the mixture, resulting in 200.01 grams of final mixture. The mixture was mixed for 10 minutes, until all of the ingredients had been thoroughly mixed.

The final mixture was molded into the final product and allowed to set-up. The resultant product contained 4.34% acetaminophen.

Example #14

Preparation of 31.50% Calcium Carbonate Semi-solid Molded Composition 19.00 grams of cocoa butter, 0.34 grams of lecithin, 1.00 grams of sorbitan monostearate, and 0.08 grams of red #40 are mixed at 100° F. for 8 minutes. 2.00 grams of polyethylene glycol, 2.00 grams of glycerine and 0.20 grams of polyoxyethylene sorbitan ester is added to the mixture. The mixture is mixed for 2 minutes at 110° F. for 2 minutes. 0.20 grams of polyglycerol ester and 31.5 grams of calcium carbonate are then added and the mixture is mixed for 4 minutes at 90° F. 0.09 grams of aspartame, 0.06 grams of acesulfame K and 42.73 grams of sugar 10× are added and the mixture is mixed for 8 minutes at 90° F. The mixture is removed from the heat and 0.60 gram of strawberry flavoring and 0.20 grams of vanilla flavorings are added, resulting in 100.00 grams of final mixture. The mixture is mixed for 10 minutes, until all of the ingredients have been thoroughly mixed.

The final mixture is molded into the final product and allowed to set-up. The resultant product contains 31.50% calcium carbonate.

Example #15

Preparation of 31.50% Calcium Carbonate Semi-solid Molded Composition 15.00 grams of cocoa butter, 1.00 grams of sorbitan monostearate, and 0.08 grams of red #40 are mixed at 100° F. for 8 minutes. 0.80 grams of polyoxyethylene sorbitan ester is added to the mixture. The mixture is mixed for 2 minutes at 110° F. for 2 minutes. 31.5 grams of calcium carbonate are then added and the mixture is mixed for 4 minutes at 90° F. 51.00 grams of xylitol are added and the mixture is mixed for 8 minutes at 90° F. The mixture is removed from the heat and 0.40 gram of strawberry flavoring and 0.22 grams of vanilla flavorings are added, resulting in 100.00 grams of final mixture. The mixture is mixed for 10 minutes, until all of the ingredients have been thoroughly mixed.

The final mixture is molded into the final product and allowed to set-up. The resultant product contains 31.50% calcium carbonate.

Example #16

Preparation of 31.50% Calcium Carbonate and 13.57% Acetaminophen Semi-solid Molded Composition 15.00 grams of cocoa butter, 0.40 grams of lecithin, and 1.00 grams of sorbitan monostearate, are mixed at 100° F.

for 8 minutes. 0.20 grams of polyoxyethylene sorbitan ester is added to the mixture. The mixture is mixed for 2 minutes at 110° F. for 2 minutes. 0.20 grams of polyglycerol ester and 31.50 grams of calcium carbonate are then added and the mixture is mixed for 4 minutes at 90° F. 0.15 grams of aspartame, 13.57 grams of coated acetaminophen microcaps (coated, 90% acetaminophen) and 37.18 grams of sugar 10× are added and the mixture is mixed for 8 minutes at 90° F. The mixture is removed from the heat and 0.80 grams of strawberry flavoring are added, resulting in 100.00 grams of final mixture. The mixture is mixed for 10 minutes, until all of the ingredients have been thoroughly mixed.

The final mixture is molded into the final product and allowed to set-up. The resultant product contains 31.50% calcium carbonate and 13.57% acetaminophen.

Example #17

Preparation of 13.57% Acetaminophen Semi-solid Molded Composition 19.00 grams of cocoa butter, 0.34 grams of lecithin, 1.00 grams of sorbitan monostearate, and 0.08 grams of red #40 are mixed at 100° F. for 8 minutes. 2.00 grams of polyethylene glycol are added to the mixture. The mixture is mixed for 2 minutes at 110° F. for 2 minutes. 13.57 grams of coated acetaminophen microcaps (coated, 90% acetaminophen) are then added and the mixture is mixed for 4 minutes at 90° F. 0.15 grams of aspartame and 63.26 grams of sugar 10× are added and the mixture is mixed for 8 minutes at 90° F. The mixture is removed from the heat and 0.40 gram of strawberry flavoring and 0.20 grams of vanilla flavorings are added, resulting in 100.00 grams of final mixture. The mixture is mixed for 10 minutes, until all of the ingredients have been thoroughly mixed.

The final mixture is molded into the final product and allowed to set-up. The resultant product contains 13.57% acetaminophen.

Example #18

Preparation of 4.34% Acetaminophen Semi-solid Molded Composition 19.00 grams of cocoa butter, 0.34 grams of lecithin, 1.00 grams of sorbitan monostearate, and 0.08 grams of red #40 are mixed at 100° F. for 8 minutes. 2.00 grams of polyethylene glycol is added to the mixture. The mixture is mixed for 2 minutes at 110° F. for 2 minutes. 0.20 grams of polyglycerol ester and 4.34 grams of coated acetaminophen microcaps (coated, 90% acetaminophen) are then added and the mixture is mixed for 4 minutes at 90° F. 0.15 grams of aspartame and 72.19 grams of sugar 10× are added and the mixture is mixed for 8 minutes at 90° F. The mixture is removed from the heat and 0.50 grams of strawberry flavoring and 0.20 grams of vanilla flavorings are added, resulting in 100.00 grams of final mixture. The mixture is mixed for 10 minutes, until all of the ingredients have been thoroughly mixed.

The final mixture is molded into the final product and allowed to set-up. The resultant product contains 4.34% acetaminophen.

Example #19

Preparation of 10.50% Ibuprofen Semi-solid Molded Composition 19.00 grams of cocoa butter, 0.34 grams of lecithin, 1.00 grams of sorbitan monostearate, and 0.08 grams of red #40 are mixed at 100° F. for 8 minutes. 2.00 grams of polyethylene glycol, 2.00 grams of glycerine and 0.20 grams of polyoxyethylene sorbitan ester is added to the mixture. The mixture is mixed for 2 minutes at 110° F. for 2 minutes. 0.20 grams of polyglycerol ester and 10.50 grams of coated ibuprofen microcaps (coated, 50% ibuprofen) are then added and the mixture is mixed for 4 minutes at 90° F. 0.15 grams of aspartame and 62.13 grams of sugar 10× are added and the mixture is mixed for 8 minutes at 90° F. The mixture is removed from the heat and 0.60 gram of strawberry flavoring, 0.20 grams of vanilla flavoring and 1.60 grams of fruit flavoring are added, resulting in 100.00 grams of final mixture. The mixture is mixed for 10 minutes, until all of the ingredients have been thoroughly mixed.

The final mixture is molded into the final product and allowed to set-up. The resultant product contains 10.50% ibuprofen.

Example #20

Preparation of 125/32 mg Dose Amoxicillin and Clavulanate Potassium Semi-solid Molded Composition The inventive subject matter containing amoxicillin and clavulanate potassium and can be made by the following process. 60.00 grams of cocoa butter, 2.00 grams of lecithin, 4.40 grams of sorbitan monostearate, and 24.00 grams of kaomel are mixed at 100° F. for 8 minutes. 12.00 grams of MCT oil and 0.80 grams of Polysorbate 80 are added to the mixture. The mixture is mixed for 2 minutes at 110° F. 0.20 grams of sodium laurel sulfate and 125 mg of amoxicillin and 32 mg of clavulanic acid as the potassium salt are then added and the mixture is mixed for 4 minutes at 90° F. 1.20 grams of aspartame and 263.60 grams of sugar 10× are added and the mixture is mixed for 8 minutes at 90° F. The mixture is removed from the heat and 0.10 grams of light green coloring (0.01 grams of 0.0025% Blue #1 and 0.09 grams of 0.0225% Yellow #5), 1.80 grams of vanilla flavoring, 0.40 grams of flavor enhancer, 2.00 grams of natural cream powder and 13.32 grams of instant release peppermint are added, resulting in 400.00 grams of final mixture. The mixture is mixed for 10 minutes, until all of the ingredients have been thoroughly mixed.

The final mixture is molded into the final product and allowed to set-up. The final product is then cut into 200 evenly-sized pieces. Each piece of product contains 125 mg amoxicillin and 32 mg of clavulanic acid.

The inventive subject matter being thus described, it will be obvious that the same may be varied in many ways. Such variations are not to be regarded as a departure from the spirit and scope of the inventive subject matter, and all such modifications are intended to be included within the scope of the following claims.

What is claimed is:

1. A rapid melt, semi-solid molded composition comprising:
   at least one binder in an amount from about 0.01% to about 70% by weight;
   a salivating agent in an amount from about 0.05% to about 15% by weight;
   a diluent/bulking material in an amount from about 10% to about 90% by weight; and
   a therapeutically effective amount of an antibiotic.
2. The composition of claim 1, wherein said antibiotic is selected from the group consisting of amoxicillin and clavulanate potassium, ciprofloxacin HCl, azithromycin, clarithromycin, sterile ceftriaxone sodium, cefuroxime axetil, imipenem cilastatin, levofloxacin, ceftazidime, ampicillin sodium and sulbactum sodium, cefaclor, amoxicillin, cefdinir, roxithromycin, sterile cefotaxime sodium, vancomycin, piperacillin sodium and tazobactum sodium, morniflumate, flomoxef sodium, cefotiam dihydrochloride, ofloxacin, mupirocin calcium, vancomycin HCl, teicoplanin, cefadroxil monohydrate, sulbactum cefoperazone, meropenem, ofloxacin, cephalexin, cefepime HCl, cefuroxime sodium, minocycline HCl, cefaclor, cefazolin, trimethoprim and sulfamethoxazole, norfloxacin, trovafloxacin, cefpodoxime proxetil, cefdinir, cefixime, panipenem, ceftibuten, levofloxacin, cefoxopran HCl, amikacin sulfate, aztreonam, minocycline HCl, ticarcillin disodium or mixtures thereof.

3. The composition of claim 2, wherein said antibiotic is amoxicillin and clavulanate potassium.

4. A method of preparing a rapid-melt, semi-solid molded composition comprising the steps of:
   a) melting at least one binder in an amount from about 0.01% to about 70% by weight with a salivating agent in an amount from about 0.05% to about 15% by weight, to form a mixture;
   b) mixing a therapeutically effective amount of an antibiotic with said mixture to form an active mixture;
   c) mixing a diluent/bulking material with said active mixture to form a final mixture; and
   d) molding said final mixture into said rapid-melt, semi-solid molded composition.

5. The method of claim 4, wherein said antibiotic is selected from the group consisting of amoxicillin and clavulanate potassium, ciprofloxacin HCl, azithromycin, clarithromycin, sterile ceftriaxone sodium, cefuroxime axetil, imipenem cilastatin, levofloxacin, ceftazidime, ampicillin sodium and sulbactum sodium, cefaclor, amoxicillin, cefdinir, roxithromycin, sterile cefotaxime sodium, vancomycin, piperacillin sodium and tazobactum sodium, morniflumate, flomoxef sodium, cefotiam dihydrochloride, ofloxacin, mupirocin calcium, vancomycin HCl, teicoplanin, cefadroxil monohydrate, sulbactum cefoperazone, meropenem, ofloxacin, cephalexin, cefepime HCl, cefuroxime sodium, minocycline HCl, cefaclor, cefazolin, trimethoprim and sulfamethoxazole, norfloxacin, trovafloxacin, cefpodoxime proxetil, cefdinir, cefixime, panipenem, ceftibuten, levofloxacin, cefoxopran HCl, amikacin sulfate, aztreonam, minocycline HCl, ticarcillin disodium or mixtures thereof.

6. The method of claim 4, wherein said antibiotic is amoxicillin and clavulanate potassium.

7. A method for treating a bacterial infection comprising the step of administering to a geriatric or pediatric patient in need thereof a pharmaceutical composition comprising:
   at least one binder in an amount from about 0.01% to about 70% by weight;
   a salivating agent in an amount from about 0.05% to about 15% by weight;
   a diluent/bulking material in an amount from about 10% to about 90% by weight;
   a therapeutically effective amount of an antibiotic.

8. The method of claim 7, wherein said antibiotic is amoxicillin and clavulanate potassium.

* * * * *